United States Patent
Aribert et al.

(10) Patent No.: US 11,117,844 B2
(45) Date of Patent: Sep. 14, 2021

(54) METHOD FOR DEHYDRATING ALCOHOLS TO OBTAIN OLEFINS, INVOLVING A STEP OF CATALYST SELECTIVATION

(71) Applicants: TOTAL RESEARCH & TECHNOLOGY FELUY, Seneffe (BE); IFP Energies Nouvelles, Rueil-Malmaison (FR)

(72) Inventors: Nicolas Aribert, Moirans (FR); Vincent Coupard, Villeurbanne (FR); Nikolai Nesterenko, Nivelles (BE); Christophe Thille, Weerde (BE); Julie Mounier, Vienne (FR)

(73) Assignees: Total Research & Technology Feluy, Seneffe (BE); IFP Energies Nouvelles, Rueil-Malmaison (FR)

( * ) Notice: Subject to any disclaimer, the term of this patent is extended or adjusted under 35 U.S.C. 154(b) by 0 days.

(21) Appl. No.: 16/629,620

(22) PCT Filed: Jul. 10, 2018

(86) PCT No.: PCT/EP2018/068613
§ 371 (c)(1),
(2) Date: Jan. 9, 2020

(87) PCT Pub. No.: WO2019/011892
PCT Pub. Date: Jan. 17, 2019

(65) Prior Publication Data
US 2021/0078918 A1 Mar. 18, 2021

(30) Foreign Application Priority Data
Jul. 10, 2017 (FR) ...................... 1756515

(51) Int. Cl.
*C07C 1/24* (2006.01)
*C07C 11/09* (2006.01)

(52) U.S. Cl.
CPC ............... *C07C 1/24* (2013.01); *C07C 11/09* (2013.01)

(58) Field of Classification Search
CPC .................. C07C 1/24; C07C 11/09
See application file for complete search history.

(56) References Cited

U.S. PATENT DOCUMENTS

| 5,059,738 | A | * | 10/1991 | Beech, Jr. | ............... | B01J 29/90 585/469 |
| 2003/0125598 | A1 | * | 7/2003 | Chisholm | ............... | B01J 38/12 585/640 |
| 2013/0204057 | A1 | | 8/2013 | Adam et al. | | |
| 2017/0341996 | A1 | * | 11/2017 | Vivien | ............... | B01J 29/65 |

FOREIGN PATENT DOCUMENTS

WO 2011/113834 A1 9/2011

OTHER PUBLICATIONS

International Search Report dated Oct. 10, 2018 issued in corresponding PCT/EP2018/068613 application (2 pages).

* cited by examiner

*Primary Examiner* — Youngsul Jeong
*Assistant Examiner* — Jason Y Chong
(74) *Attorney, Agent, or Firm* — Millen, White, Zelano & Branigan, P.C.; John A. Sopp

(57) ABSTRACT

The invention relates to a process for dehydrating alcohols to olefins, comprising a reaction step and a catalyst selectivation step.

12 Claims, 1 Drawing Sheet

Heat profiles in the catalytic bed measured before, during and after the 70-minute selectivation step.

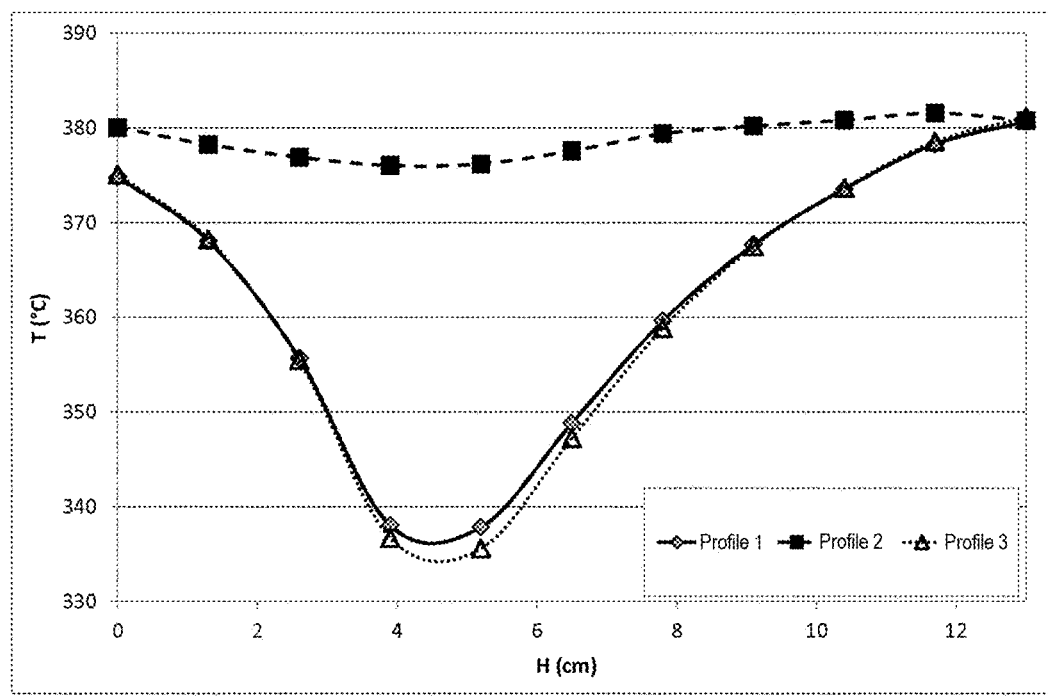
Figure 1: Heat profiles in the catalytic bed measured before, during and after the 70-minute selectivation step.
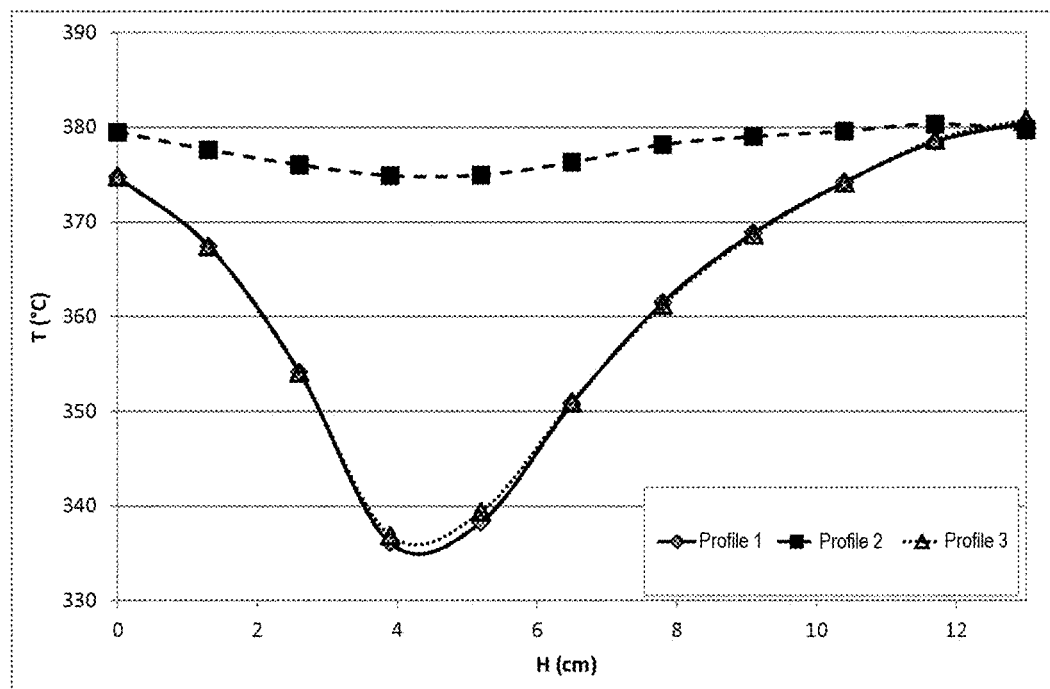
Figure 2: Heat profiles in the catalytic bed measured before, during and after the 25-minute selectivation step.

METHOD FOR DEHYDRATING ALCOHOLS TO OBTAIN OLEFINS, INVOLVING A STEP OF CATALYST SELECTIVATION

TECHNICAL FIELD OF THE INVENTION

The present invention relates to a process for dehydrating alcohols to olefins. The feedstock for the process may be obtained via chemical processes or via fermentation processes. This process uses a shaped catalyst based on a zeolite comprising at least one series of channels, the opening of which is defined by a ring of 8 oxygen atoms (8 MR) and comprises a step making it possible to improve the selectivity of the catalyst.

The alkenes obtained, in particular isobutene, 1-butene and 2-butenes, are of great value in the field of the petrochemical industry and of organic synthesis.

PRIOR ART

EP 2348005 describes the dehydration of alcohols containing from 2 to 10 carbon atoms to the corresponding olefin on an FER zeolite catalyst with an Si/Al atomic ratio of less than 100. The weight hourly space velocity (WHSV) relative to the alcohol is at least 4 h$^{-1}$ and the temperature is from 320 to 600° C.

WO 2011/113834 describes the simultaneous dehydration and skeletal isomerization of isobutanol in the presence of crystalline silicate catalysts with a mean channel size (10 MR), which are optionally dealuminated and optionally phosphorus-modified, of the FER, MWW, EUO, MFS, ZSM-48, MTT, MFI, MEL or TON group having an Si/Al ratio greater than 10, silicoaluminophosphate molecular sieves of the AEL group, or silica-, zirconia-, titania- or fluoro-alumina on zeolite catalysts. The WWH (ratio of the mass flow of feedstock to the mass of catalyst, corresponding to the WHSV) relative to the alcohol is at least 1 h$^{-1}$ and the temperature is from 200 to 600° C. The maximum proportion of n-butenes reached in the butenes is 58.4% at 375° C. with a high WWH (12.6 h$^{-1}$) on an FER zeolite powder of Si/Al 33. No notion of stability of the performance as a function of the time with feedstock is mentioned in said document. The only other catalyst illustrated is gamma-alumina.

The catalytic performances (conversion and selectivity toward the formation of linear olefins) decrease as a function of the operating time of the process, mainly due to the formation of coke during the isomerizing dehydration reaction. In order to maintain the conversion target, the mean reaction temperature is increased, bringing about reductions in selectivity. Thus, a regeneration step is necessary when either the maximum admissible reaction temperature is reached, or the selectivity toward isoolefins exceeds a set value which no longer allows the process to be economically viable.

The regeneration step corresponds mainly to a step of combustion of the coke formed in air and at elevated temperature, described in numerous documents. For example, EP 3040125 describes the regeneration of the catalyst by combustion of the coke formed at the surface. Benito et al. (Ind. Eng. Chem. Res., 1996, 35, 2177-2182) describe reaction-regeneration cycles, the regeneration being performed by combustion.

However, this step gives rise to substantial additional costs in the process for manufacturing linear olefins.

Since the selectivity toward linear olefins often decreases faster than the conversion toward values leading to performing a regeneration, it is often this factor which leads to launching a catalyst regeneration operation. A particular process for improving the selectivity and the stability of the catalyst has been discovered by the Applicant. This improvement makes it possible to delay the recourse to regeneration when said regeneration is conditioned by the exceeding of the isobutene/butene selectivity target.

Subject and Advantage of the Invention

The invention relates to a process for dehydrating alcohols to olefins, comprising:
a) a reaction step fed with a feedstock comprising at least one alcohol, said reaction step being performed in the gas phase at a weighted average temperature of between 250 and 400° C., at a pressure of between 0.2 MPa and 1 MPa and at a WWH of between 1 and 18 h$^{-1}$ in the presence of a catalyst comprising a zeolite comprising at least one series of channels whose opening is defined by a ring of 8 oxygen atoms (8 MR) producing an olefin effluent;
b) a selectivation step comprising, for a period of between 0.5 and 5 hours, stoppage of the feed and maintenance of the temperature and pressure of said step a);
c) resumption of the feed on conclusion of step b) with return to the conditions of step a);
said selectivation step being performed when the selectivity toward isoolefins n of said step a) is greater than 25%, or when the conversion into alcohols of said step a) is less than 99%.

The process according to the invention is directed toward mainly producing linear olefins. Surprisingly, the process according to the invention makes it possible to significantly improve the selectivity toward linear butenes in the olefin effluent without modifying the catalytic activity, i.e. while maintaining the conversion into alcohols.

DETAILED DESCRIPTION OF THE INVENTION

Reaction Step a)

The process according to the invention comprises a reaction step a) fed with a feedstock comprising at least one alcohol, said reaction step being performed in the gas phase at a weighted average temperature of between 250 and 400° C., at a pressure of between 0.2 MPa and 1 MPa and at a WWH of between 1 and 18 h$^{-1}$ in the presence of a catalyst comprising a zeolite comprising at least one series of channels whose opening is defined by a ring of 8 oxygen atoms (8 MR) producing an olefin effluent.

Feedstock

The feedstock treated in the process according to the invention is a feedstock comprising at least one alcohol, advantageously at least one primary monoalcohol of formula R—CH$_2$—OH, in which R is a nonlinear alkyl radical of general formula C$_n$H$_{2n+1}$ where n is an integer between 3 and 20, preferably between 3 and 10, preferably between 3 and 5. Said reaction step a) is a step in which the alcohol is dehydrated to olefin, branched alcohols advantageously being dehydrated to linear olefins. The process according to the invention is advantageously an isomerizing dehydration process.

Preferably, the feedstock comprises from 40% to 100% by weight, preferentially from 70% to 100% by weight, advantageously from 85% to 100% by weight of at least one alcohol, advantageously of at least one primary monoalcohol as defined previously.

Among the primary monoalcohols that may be used in the process according to the invention, mention may be made of isobutanol, 2-methylbutan-1-ol, 2,2-dimethylpropan-1-ol, 2-methylpentan-1-ol, 2,2-dimethylbutan-1-ol and 2-ethylbutan-1-ol. Said feedstock may comprise one or more primary monoalcohols.

Said primary monoalcohol is preferentially isobutanol or 2-methyl-1-butanol, taken alone or as a mixture. Very preferentially, said primary monoalcohol is isobutanol.

Said feedstock may originate from chemical or biochemical processes, for example fermentation processes. In particular, this feedstock may be derived from lignocellulosic biomass fermentation processes.

Said feedstock may contain water, advantageously up to 60% by weight of water, preferentially up to 70% by weight, very advantageously up to 15% by weight. It may also comprise impurities of mineral type (such as Na, Ca, P, Al, Si, K, $SO_4$) and of organic type (such as methanol, ethanol, n-butanol, aldehydes, ketones and the corresponding acids, for example furanic, acetic or isobutyric acid).

Said reaction step is performed in the gas phase, at a weighted average temperature of between 250 and 400° C., preferably between 250 and 375° C., at a pressure of between 0.2 MPa and 1 MPa and at a WWH of between 1 and 18 $h^{-1}$ in the presence of a catalyst comprising a zeolite comprising at least one series of channels whose opening is defined by a ring of 8 oxygen atoms (8 MR).

The term "WWH" means the "weight per weight per hour", i.e. the mass flow of alcohol in the feedstock at the reactor inlet divided by the mass of catalyst in said reactor. This concept is also sometimes denoted under the acronym WHSV or "weight hourly space velocity".

The term "weighted average temperature" (denoted by WAT) means the average temperature in the catalytic bed, the bed being all of the beds present in the reactor, in which beds the catalytic reaction takes place, calculated along the axis of flow through said bed. Namely a bed of length L and of surface area S, the reactive mixture flowing along the longitudinal axis x of this bed, the inlet into the catalytic bed forming the origin of the axis (x=0), the weighted average temperature, denoted by WAT, is expressed according to the following formula:

$$WAT = \frac{1}{L}\int_0^L T(x)dx$$

Since the reaction is endothermic and the reactor operates either in isothermal mode, or in adiabatic mode, the weighted average temperature is representative of the reaction temperature. The heat input is performed by any heating means known to a person skilled in the art.

The reaction takes place in one or more reactors, each reactor being operated under identical conditions. The WAT of each of the reactors is adjusted to a value between 250° C. and 400° C., preferably between 250 and 375° C. Thus, in the following description, the term "the reactor" denotes both the reactor of this step when this step comprises only one reactor, and each of the reactors of this step, when this step comprises more than one reactor.

Said catalyst is positioned in one or more fixed beds, which may be operated in upflow, downflow or radial flow.

Before coming into contact with the feedstock to be treated, the catalyst is activated by any means known to a person skilled in the art, for example by heat treatment in air.

Catalyst

In accordance with the invention, the catalyst used in said reaction step a) comprises a zeolite having at least one series of channels, the opening of which is defined by a ring of 8 oxygen atoms (8 MR) as defined in the classification "Atlas of Zeolite Structure Types, Ch. Baerlocher, L. B. Mc Cusker, D. H. Olson, 6th Edition, Elsevier, 2007, Elsevier".

According to a particular embodiment, the zeolite may also advantageously contain at least one series of channels, the pore opening of which is defined by a ring containing 10 oxygen atoms (10 MR).

Said zeolite is advantageously chosen from zeolites having 8 and 10 MR channels such as zeolites of FER and MFS structural type, taken alone or as a mixture. The zeolite is more advantageously chosen, for the FER type, from the group consisting of ferrierite, FU-9, ISI-6, NU-23 and ZSM-35 zeolites, and, for the MFS type, the ZSM-57 zeolite, and mixtures thereof. Said zeolite is very advantageously of FER type and preferably ferrierite. Preferably, said zeolite consists of ferrierite.

Preferably, said zeolite is a ferrierite with an Si/Al mole ratio of from 8 to 70, preferably 10 to 70, preferably chosen between 10 and 50, preferably chosen between 20 and 50.

Said catalyst also comprises a binder.

The zeolite content in the catalyst is 55-90% by weight, preferably between 60% and 80% by weight.

The binder is advantageously chosen from a silicic binder, an $AlPO_4$, a clay, a zirconia, a titanium oxide, or SiC. Very preferably, it is a silicic binder.

The content of binder in the catalyst is between 10% and 45% by weight, preferably between 20% and 40%. The catalyst may optionally contain impurities in a small amount having no technical effect on the conversion/selectivity of the catalyst. Said catalyst may be formed by any technique known to those skilled in the art, for example in the form of powder, beads, pellets, granules or extrudates (hollow or filled cylinders, multilobal cylinders, for example with 2, 3, 4 or 5 lobes, twisted cylinders), rings, etc.

Generally, the catalyst does not comprise any metals. This term "no metals" means that there are no metals added during the preparation. It is also understood that there may be impurities in the binders and thus in small amounts. Preferably, there is no aluminum or iron in the silica.

Selectivation Step b)

The process according to the invention comprises a step b) of selectivation of the catalyst, comprising, over a period of between 0.5 and 5 hours, stoppage of the feed and maintenance of the temperature and pressure of said step a), said selectivation step being performed when the selectivity toward isoolefins n of said step a) is greater than 25%, or when the conversion into alcohols of said step a) is less than 99%.

The term "selectivity toward isoolefins n" means the mass ratio of isoolefins comprising n carbon atoms to the total amount of olefins comprising n carbon atoms present in the olefin effluent obtained from step a). The selectivity toward isoolefins n increases gradually during step a) of the process according to the invention.

The conversion of the alcohol is calculated in the following manner:

$$Conversion_{alcohol} = \left(1 - \frac{\sum_{alcohol} m_{alcohol\ outlet}}{\sum_{alcohol} m_{alcohol\ inlet}}\right) \times 100$$

More specifically, in the case where the alcohol is isobutanol:

$$Conversion_{iC4OH} = \left(1 - \frac{m_{iC4OH\ outlet}}{m_{iC4OH\ inlet}}\right) \times 100$$

The compositions at the inlet and outlet of the reaction step required for calculating the selectivities and conversions are determined by methods that are well known to those skilled in the art, for example by sampling and analysis, in particular by gas chromatography analysis, the sampling possibly being performed continuously or sporadically, at time intervals allowing monitoring of the evolution of the selectivity and/or conversion values, this interval being readily determined by a person skilled in the art (for example every minute, every 5 minutes, every 10 minutes, every 30 minutes or every hour).

The Applicant has discovered that the stoppage of the feed performed in conjunction with maintenance of the temperature and pressure of said step a) for a period of between 0.5 and 5 hours, advantageously between 0.5 and 3 hours, very advantageously between 0.5 and 2 hours makes it possible to reduce the selectivity toward isoolefins while at the same time maintaining at least the conversion of the alcohol into olefins once the feed has restarted on conclusion of the period of stoppage and once the conditions of step a) have been re-established.

The maintenance of the temperature and pressure may be performed by any means known to a person skilled in the art. For example, maintenance of the pressure may be performed by reducing, or even stopping, the production of effluent from said reaction step, or else by adding an inert fluid, for instance nitrogen.

Advantageously, said selectivation step b) also comprises stoppage of effluent production from said reaction step a).

When said step b) is performed for a time of less than 0.5 hour, no effect is observed. On the other hand, prolonged stoppage beyond 5 hours leads to the formation of undesirable products at the surface of the catalyst, which harm the performances of the process.

Step c) of Resumption of the Feed

The process according to the invention comprises a step c) of resumption of the feed on conclusion of step b) with return to the conditions of step a).

At the end of the period of stoppage of the feed in accordance with step b) of the process according to the invention, the feed is resumed in order to return to the conditions of step a) of said process. At the end of step b), the process according to the invention thus functions in accordance with the features of step a) of the process according to the invention, the selectivity toward isoolefin n having been reduced.

DESCRIPTION OF THE FIGURES

FIGS. 1 and 2 show the axial temperature profiles in the reactor before the reaction step a) (profile 1), during the reaction step a) (profile 2) and after the selectivation step b) once the feeding of the feedstock has been resumed (profile 3).

EXAMPLES

Description of the catalytic test unit used for examples 1 and 2.

The dehydration step is performed in a catalytic test unit comprising a fixed bed operating in downflow mode. The catalyst is loaded into a 316L stainless-steel reactor to a height of 13 cm. The catalyst is then activated at 450° C. under 24 Nl/h of air for a stage of two hours after a temperature increase of 50° C./hour. The temperature is then lowered to the test temperature under 500 Nl/h of nitrogen in order to remove the air present in the system before injection of the alcohol feedstock.

The feedstock is vaporized in a preheating oven at 150-200° C. upstream of the reactor and then injected into the catalytic reactor. The operating conditions are as follows: weighted average temperature of 362° C., WWH (weight of feedstock per weight of catalyst per gram) of 8.5 $h^{-1}$.

At the reactor outlet, the total effluent passes via two separators, one operating at the reaction pressure and the other at low pressure, in order to recover, on the one hand, an olefin-rich effluent gas and a water-rich liquid phase. Analysis of the gaseous effluent is performed on an on-line gas chromatograph equipped with two columns. Analysis of the liquid effluent is performed on a delocalized machine by gas chromatography. These analyses make it possible to determine the isobutanol conversion, the selectivities toward various products and notably the selectivity toward isobutene and the fraction of linear butenes in the reaction effluent, which fraction it is desired to maximize. The analyzers also make it possible to measure the selectivity toward side products such as propene or products containing five or more carbon atoms.

Isobutanol Conversion:

This indicator makes it possible to evaluate the activity of the catalyst.

$$Conversion_{iC4OH} = \left(1 - \frac{m_{iC4OH\ outlet}}{m_{iC4OH\ inlet}}\right) \times 100$$

Selectivity Toward Isobutene in the C4 Olefinic Fraction

In order to measure the isomerization of the olefinic effluent, an indicator based on the amount (as mass of equivalent carbon) of linear butenes formed was defined.

$$Selectivity_{isobutene} = \left(\frac{isobutene\ mass_{outlet}}{butene\ mass_{outlet}}\right) \times 100$$

Example 1 (in Accordance): 70-Minute Procedure, Sufficient Time

In this example, stoppage of the feed is performed for 70 minutes, the other operating conditions being maintained. The selectivity toward isobutene is reduced.

A feedstock comprising 95% by weight of isobutanol and 5% by weight of water is fed into the reactor inlet with a WWH of 8.5 $h^{-1}$. The reaction step is performed at a pressure of 0.9 MPa and a weighted average temperature (WAT) of 362° C.

After a time of 60 hours with feedstock, the selectivity toward isobutene in the olefinic effluent reaches 23.9%. The feeding of feedstock and the withdrawal of olefinic effluent are interrupted. The temperature and pressure are maintained in the reaction step.

Temporary stoppage of the flow of feedstock is performed for 70 minutes. After resuming the feeding of the feedstock under the same conditions as initially (WWH of 8.5 $h^{-1}$), the selectivity toward isobutene in the olefinic effluent is 19.3%, i.e. a difference of 4.6 points.

The isobutanol conversion is greater than 99.95%, identical to the conversion before stoppage.

FIG. 1 shows the axial temperature profiles in the reactor before the reaction step a) (profile 1), during the reaction step a) (profile 2) and after the selectivation step b) once the feeding of the feedstock has been resumed and the conditions in accordance with step a) have been stabilized (profile 3) after stoppage of the feed for 70 minutes. The x-axis shows the total height of the reactor. The y-axis shows the temperature in the reactor.

It is observed in FIG. 1 that the heat profiles before and after the selectivation step (profile 1 and profile 3) are substantially the same. This gain is therefore not due to a modification of the heat profile within the reaction step.

Example 2 (not in Accordance): 25-Minute Procedure, Insufficient Time

In this example, stoppage of the feed is performed for 25 minutes, the other operating conditions being maintained. The selectivity toward isobutene is not modified.

A feedstock comprising 95% by weight of isobutanol and 5% by weight of water is fed into the reactor inlet with a WWH of 8.5 $h^{-1}$. The reaction step is performed at a pressure of 0.9 MPa and a WAT of 362° C.

After a time of 30 hours with feedstock, the selectivity toward isobutene in the olefinic effluent reaches 24.0%. The feeding of feedstock and the withdrawal of olefinic effluent are interrupted. The temperature and pressure are maintained in the reaction step.

Temporary stoppage of the flow of feedstock is performed for 25 minutes. After resuming the feeding of the feedstock under the same conditions as initially (WWH of 8.5 $h^{-1}$), the selectivity toward isobutene in the olefinic effluent is 23.8%, i.e. an insignificant difference of 0.2 point which is within the measurement error.

The isobutanol conversion is greater than 99.95%, identical to the conversion before stoppage.

FIG. 2 shows the axial temperature profiles in the reactor before the reaction step a) (profile 1), during the reaction step a) (profile 2) and after the selectivation step b) once the feeding of the feedstock has been resumed and the conditions in accordance with step a) have been stabilized (profile 3) after stoppage of the feed for 25 minutes. The x-axis shows the total height of the reactor. The y-axis shows the temperature in the reactor.

It is observed in FIG. 2 that the heat profiles before and after selectivation are substantially the same. This gain is therefore not due to a modification of the heat profile within the reaction step.

It is moreover observed in FIG. 2 that the temperature profile during the selectivation step is similar to that obtained in example 1. The effect observed is therefore not due to a simple rise in temperature of the bed during the selectivation step.

Example 3 (not in Accordance): 6-Hour Procedure

In this example, stoppage of the feed is performed for 6 hours, the other operating conditions being maintained.

A feedstock comprising 95% by weight of isobutanol and 5% by weight of water is fed into the reactor inlet with a WWH of 8.5 $h^{-1}$. The reaction step is performed at a pressure of 0.9 MPa and a WAT of 366° C.

After a time of 80 hours with feedstock, the selectivity toward isobutene in the olefinic effluent reaches 23.8% and the isobutanol conversion is greater than 99.94%. The feeding of feedstock and the withdrawal of olefinic effluent are interrupted. The temperature and pressure are maintained in the reaction step.

Temporary stoppage of the flow of feedstock is performed for 6 hours.

After resuming the feeding of the feedstock under the same conditions as initially (WWH of 8.5 $h^{-1}$), the selectivity toward isobutene in the olefinic effluent is 19%.

The isobutanol conversion is 97.53%.

After stoppage of the flow of feedstock for 6 hours, a decrease in the isobutanol conversion from 99.94% to 97.53% is observed. This reduction in the isobutanol conversion reveals a significant loss of activity of the catalyst.

The invention claimed is:

1. A process for dehydrating alcohols to olefins, comprising:
   a) a reaction step comprising reacting a feedstock comprising at least one alcohol in the gas phase under operating conditions including a weighted average temperature of between 250 and 400° C., a pressure of between 0.2 MPa and 1 MPa and a WWH (weight of alcohol in the feedstock per weight of catalyst per gram) of between 1 and 18 $h^{-1}$, in the presence of a catalyst comprising a zeolite comprising at least one series of channels the opening of which is defined by a ring of 8 oxygen atoms (8 MR), to produce an olefin effluent and a spent catalyst;
   b) a catalyst selectivation step comprising, for a period of between 0.5 and 5 hours, stopping the flow of the feedstock and maintaining the temperature and pressure of said step a) in the presence of the spent catalyst to obtain a selectivated catalyst; and
   c) resuming the flow of the feedstock in the presence of the selectivated catalyst on conclusion of step b) under the operating conditions of step a);
   wherein said catalyst selectivation step is performed when the selectivity toward isoolefins n in said step a) is greater than 25%, where said isoolefins n are isoolefins comprising n carbon atoms and n ranges from 4 to 21, or when the conversion of the at least one alcohol in said step a) is less than 99%, and
   wherein the catalyst is not subject to regeneration by combustion and/or regeneration fluid between the end of step a) and the beginning of step c).

2. The process as claimed in claim 1, in which said feedstock comprises from 40% to 100% by weight of at least one alcohol.

3. The process as claimed in claim 1, in which said feedstock comprises at least one primary monoalcohol of formula R—$CH_2$—OH, in which R is a nonlinear alkyl radical of general formula $C_nH_{2n+1}$ where n is an integer between 3 and 20.

4. The process as claimed in claim 3, in which said primary monoalcohol is isobutanol or 2-methyl-1-butanol, taken alone or as a mixture.

5. The process as claimed in claim 1, in which said zeolite also contains at least one series of channels, the pore opening of which is defined by a ring containing 10 oxygen atoms (10 MR).

6. The process as claimed in claim 1, in which said zeolite is chosen from zeolites having a FER and MFS framework or a mixture thereof.

7. The process as claimed in claim 6, in which said zeolite is chosen from the group consisting of ferrierite, FU-9, ISI-6, NU-23 and ZSM-35 zeolites having a FER framework, ZSM-57 zeolite having a MFS framework, and mixtures thereof.

8. The process as claimed in claim 1, in which the period of stopping the flow of the feedstock in said step b) is between 0.5 and 3 hours.

9. The process as claimed in claim 1, in which the period of stopping the flow of the feedstock in said step b) is between 0.5 and 2 hours.

10. The process as claimed in claim 1, in which said catalyst selectivation step further comprises stopping olefin effluent production of said reaction step a).

11. The process as claimed in claim 1, wherein said catalyst selectivation step is performed when the selectivity toward isoolefins n in said step a) is greater than 25%.

12. The process as claimed in claim 1, wherein said catalyst selectivation step is performed when the conversion of the at least one alcohol in said step a) is less than 99%.

\* \* \* \* \*